United States Patent [19]

Polyak

[11] Patent Number: 4,994,020
[45] Date of Patent: Feb. 19, 1991

[54] IMPLANTABLE ARTIFICIAL SPHINCTER SYSTEM

[75] Inventor: Mark Polyak, Minnetonka, Minn.

[73] Assignee: American Medical Systems, Inc., Minnetonka, Minn.

[21] Appl. No.: 383,827

[22] Filed: Jul. 21, 1989

[51] Int. Cl.5 .......................... A61F 2/02; A61F 2/08
[52] U.S. Cl. ...................................... 600/31; 623/14; 128/DIG. 25; 251/65
[58] Field of Search .................................. 600/29-31; 128/DIG. 25; 623/14, 12; 251/65

[56] References Cited

U.S. PATENT DOCUMENTS

| Re. 31,121 | 1/1983 | Reinicke | 137/493 |
|---|---|---|---|
| 3,812,841 | 5/1974 | Isaacson | 600/29 |
| 3,854,469 | 12/1974 | Giori et al. | 600/31 |
| 3,863,622 | 2/1975 | Buuck | 600/31 |
| 4,222,377 | 9/1980 | Burton | 600/31 |
| 4,417,567 | 11/1983 | Trick | 600/31 |
| 4,571,749 | 2/1986 | Fischell | 623/14 |
| 4,584,990 | 4/1986 | Haber et al. | 600/31 |
| 4,682,583 | 7/1987 | Burton et al. | 600/31 |
| 4,709,690 | 12/1987 | Haber | 600/31 |
| 4,721,509 | 1/1988 | Craggs | 623/14 |

FOREIGN PATENT DOCUMENTS 1194358  6/1970  United Kingdom ................. 600/30

Primary Examiner—Ronald Frinks
Attorney, Agent, or Firm—Peter C. Richardson; Lawrence C. Akers; Michael J. Pantuliano

[57] ABSTRACT

An implantable artificial sphincter system for reversibly occluding a body passageway, which system includes occlusion means, pump means, and the unique feature of a fluid capacitor disposed on a control assembly for the system, which is capable of increasing volume under fluid pressure. The fluid capacitor is connected with the occlusion means in such fashion that said occlusion means will remain substantially inflated during short, but significant, pressure increases, but will at least partially deflate upon the advent of prolonged but moderate pressure increases on the body passageway. While in its preferred embodiment no other fluid containing component is needed, if desired a volume compensator can also be included in the system. A valve preferably of the magnetic type can also be included for activating or deactivating the system.

32 Claims, 5 Drawing Sheets

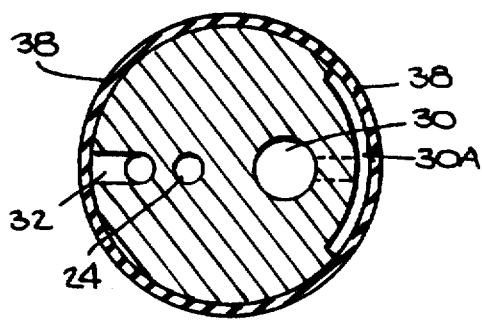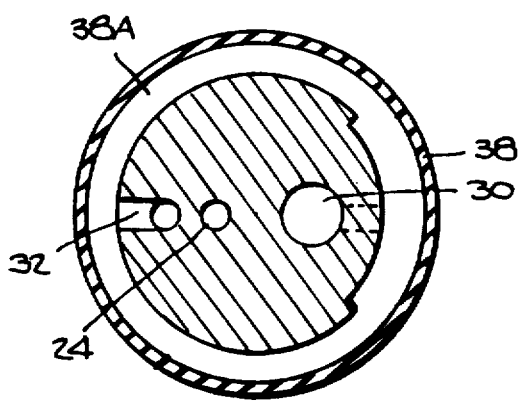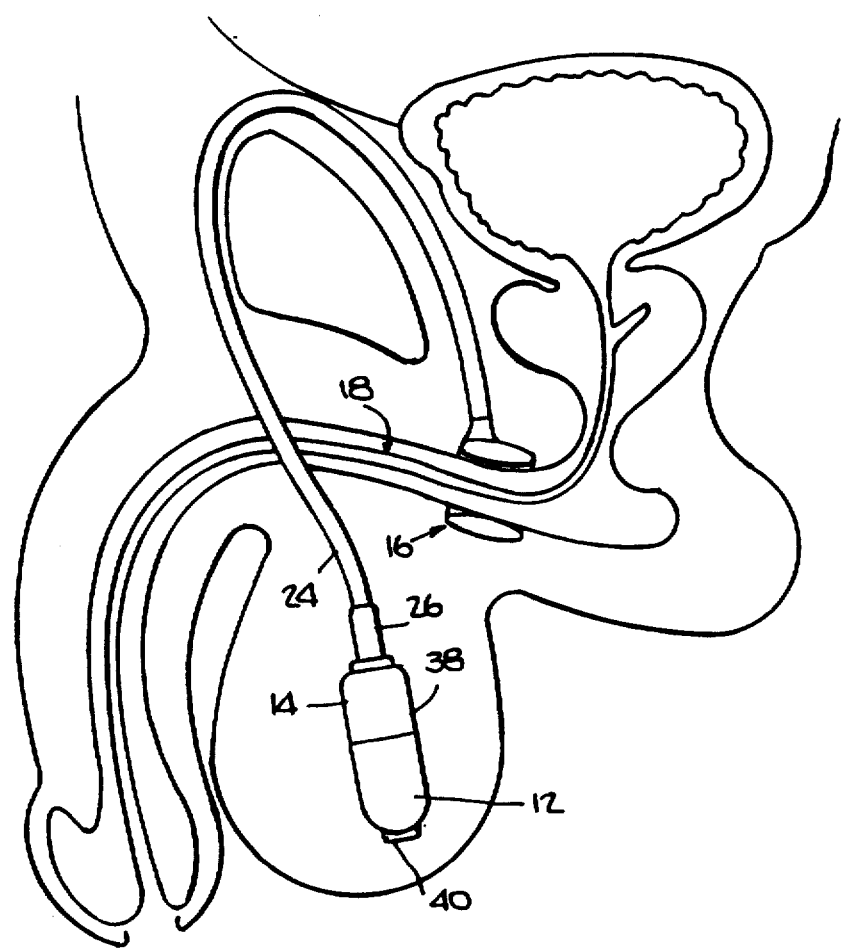

IMPLANTABLE ARTIFICIAL SPHINCTER SYSTEM

BACKGROUND OF THE INVENTION

This invention relates generally to methods and devices for treating incontinence and more specifically relates to an improved implantable artificial sphincter system for the control of excretory body passages.

The artificial sphincters for treating incontinence which are known or described in the art often employ a distally located fluid reservoir, usually of the balloon or bulb type, which in conjunction with one or more pumps serves to transfer fluid into or out of an inflatable cuff which is disposed about the body passageway to be occluded. When the cuff is inflated, the body passageway is occluded; when it is deflated the body passageway is opened and excretion occurs. It is also the norm that these basic components, that is, cuff, pump means, and reservoir are connected by means of lumens or fluid transmission passageways. Typically one fluid transmission passageway connects the cuff with the pump while a second transmission line connects the pump with the reservoir.

The location of the balloon type reservoirs are of particular concern in the known artificial sphincter systems. This is because reservoirs of this type tend to be rather large, particularly in proportion to the other components of the system. Because of their size, they are usually located in areas of the body which have room for such implantation. In most instances this will be in the abdomen. However, to implant bulb or balloon reservoirs in the abdomen necessitates rather complex surgery which can be debilitating particularly to the elderly. Moreover, abdominal surgery also incurs a fairly high risk of postoperative infection and is almost always rather long in duration, requiring a fairly lengthy postoperative healing period due to the trauma to which the body has been subjected. It is apparent that it would be highly desirable to avoid abdominal surgery and in general to reduce the complexity of the implantation procedures for artificial sphincters.

With known or described artificial sphincters it can also happen that high-intensity, short-duration (e.g., less than 5 minutes), stress-induced pressure "spikes", which occur, for example, as a consequence of the sudden onset of coughing or laughing, or other kind of stressful outburst, or even by the single act of suddenly lifting a heavy object, will often involuntarily induce the deflation of an occluding cuff. This can happen because these kinds of pressure "spikes" are often considerably above the threshold pressures necessary for the voluntary activation of the presently described sphincter systems. As a consequence, the "spike" can cause a sharp increase in pressure on the bladder and result in a surge of fluid under pressure downstream from the bladder (particularly if the latter is fairly full to begin with), which can then forcefully deflate the cuff (at least partially) and cause the urethra (or other excretory passage) to be opened and excretion to occur. This manifestation of incontinence, particularly where an artificial sphincter has been implanted, can be especially distressing and even demoralizing to an individual. It is thus also apparent that an artificial sphincter which would avoid this problem, i.e. which under these conditions would keep the cuff inflated and hence the urethra occluded, would also be very desirable.

SUMMARY OF THE INVENTION

The present invention relates to an implantable artificial sphincter system for reversibly occluding a body passageway, which system includes occlusion means, pump means, and the unique feature of a fluid capacitor disposed on a control assembly for the system, which is capable of increasing volume under fluid pressure. The fluid capacitor is connected with the occlusion means in such fashion that said occlusion means will remain substantially inflated during short, but significant, pressure increases, but will at least partially deflate upon the advent of prolonged but moderate pressure increases on the body passageway. While in its preferred embodiment no other fluid containing component is needed, if desired a volume compensator as hereinafter described can also be included in the system.

The implantable sphincter system of this invention, in its preferred form, defines a simple sphincter which includes a minimal number of components, of small size. In a preferred form, to be described hereafter, it also provides a mechanism for deactivation of the system to avoid somewhat the problems attendant with postoperative surgical trauma and sensitivity. It also provides a system of great simplicity which can be easily used by an incontinent person. It further provides a system which substantially inhibits urine reflux or bladder distension as a consequence of prolonged moderate (e.g. 60–70 cm of $H_2O$) pressure increases on the bladder, and also substantially inhibits involuntary incontinence due to short, but significant, "spike" pressures occasioned by stress, or other emotional disturbances. In male patients all of the components of the system, including the optional volume compensator, are implanted in or about the scrotum. Only the cuff which circumferentially surrounds the body passageway is in any way distally placed. No components need be implanted in the abdomen.

BRIEF DESCRIPTION OF THE DRAWINGS

FIG. 2 is a transverse cross-section along the axis 2—2 of the control assembly depicting the fluid capacitor in a nondistended form circumferentially disposed about the assembly.

FIG. 4 is a transverse cross-section, similar in all respects to FIG. 2, but showing the fluid capacitor in distended form.

FIG. 5 is an environmental view illustrating the implantable sphincter system, disposed in a male, with all components save the cuff implanted in the scrotum.

DETAILED DESCRIPTION OF THE DRAWINGS

Figure 1:
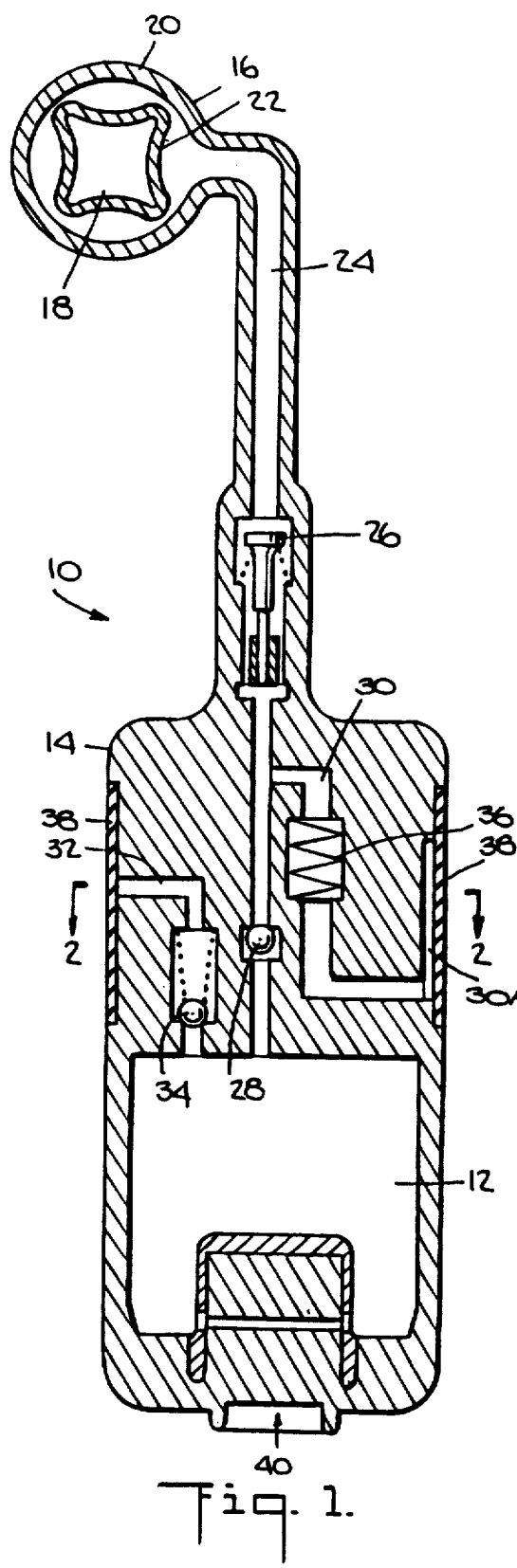
FIG. 1 illustrates an implantable sphincter system in accordance with the preferred embodiment of this invention, with cuff, pump means, control assembly, and fluid capacitor illustrated partially in vertical section.

Referring now to the drawings in more detail, there is shown in FIG. 1 an implantable artificial sphincter system 10 in accordance with the preferred embodiment of the invention. Sphincter system 10 includes a pump 12 which can be of any suitable type, but typically is of an externally activated bulb type (hereinafter to be termed "pump bulb"), a control assembly 14, and a cuff 16 which surrounds a body passage 18. The cuff 16 includes a generally non-elastic backing 20 and an inflatable inner cushion 22. The cuff 16 is in fluid communication with the pump bulb 12 by means of passageway (i.e. lumen or tube) 24. Downstream from the cuff 16 there is shown deactivation valve 26, an optional feature hereinafter further described in FIGS. 7, 8, and 9, which is preferably magnetically activated or deactivated by external means.

Further downstream in control assembly 14 is cuff check valve 28 which prevents the flow of fluid from the pump bulb 12 to the cuff 16. Also included in control assembly 14 is passageway 30 which exits, as shown, off passageway 24 and includes a fluid resistor element 36, and passageway 32 which is in fluid communication with pump bulb 12 through a check valve 34. Both passageways 30 and 32 are in fluid communication with fluid capacitor 38 which is disposed as shown along the indicated area of control assembly 14. Finally, also shown is optional feature, septum 40, which as hereinafter described can be used to have fluid inserted into or removed from the system, and to control the pressure of the system, as needed.

Because the entire sphincter is implanted into the body, all surfaces thereof are formed of a physiologically inert or biocompatible material. Illustrative of such material is silicone rubber, but any material known to be useful for artificial devices to be implanted in the body can be employed.

As with the rest of the system, the fluid capacitor 38 should also be made of a physiologically inert material, but it must be capable of increasing its volume under fluid pressure such as by being distended because of internally directed fluid pressure of a predetermined strength. As such, therefore, it is preferably a tubular membrane which will distend in accordance with preset conditions. The distensibility can be a function of thickness, or of the material, or both. Thus if the degree of distensibility is a function of thickness, it can be made of the same material as, for example, the rest of the control assembly. Alternatively it can be made of a different physiologically inert material, but it must still have suitable elasticity. As stated, this degree of distensibility can be preset or programmed into the system.

The fluid capacitor is preferably circumferentially disposed about the indicated section of the control assembly 14. This is more clearly shown in the top view, transverse cross-section depicted in FIG. 2, which is taken across the axis 2—2 of the assembly. However, it is possible for the capacitor to be disposed as sections on sides of the control assembly. In this latter form, however, there must still be fluid communication between the sections so that in essence there is still only one capacitor.

Fluid resistor or resistance element 36 provides a generally predetermined resistance to fluid flow through passageway 30 to and from capacitor 38. This element may be of several types known in the art, but typically is one of the kind which defines a labyrinth-type fluid passage such as one formed by a plurality of axially aligned, perforated disks which are adapted to define a restrictive path for fluid flow.

Valves 28 and 34 are types well known in the art. Valve 28 is typically a one-way check valve of the ball and seat type which permits fluid flow from the cuff to the pump bulb. Valve 34 is typically a ball and seal spring-biased type which permits fluid flow from the pump bulb 12 into the fluid capacitor.

In the sphincter system of this invention, the fluid pressure is predetermined and is constant throughout the system. To commence normal operation, that is, to deflate the cuff 16 and enable excretion to pass out of the body passageway (hereinafter for convenience to be referred to as the urethra), the pump bulb 12 is initially squeezed. This places the fluid thereof under pressure which forces it upstream to valve 34. Under the pressure of the fluid, the valve 34 is dislodged from its normally closed position, i.e., the counter force of the spring 34A thereof is overcome. The now open valve 34 permits the fluid to continue into narrow passageway 32 and then into capacitor 38, which distends because of its modulus of elasticity. The surge of fluid from the pump bulb also moves upstream to valve 28 which is pushed into a closed position, i.e., against the seat thereof. At this point, no fluid proceeds upstream to cuff 16 through passageway 24.

On release of the pump bulb, the resulting pressure differential caused by the pump bulb returning to its unsqueezed shape draws fluid downstream from the cuff 16. Valve 28 is then opened because the downstream pressure of fluid in passageway 24 is greater than the pressure in evacuated pump bulb 12. Fluid then passes through check valve 28 (and if present, deactivation valve 26) into pump bulb 12.

At the same time, valve 34 returns to its closed position, because the pressure of distended diaphragm 38 also is greater than that of evacuated pump 12, and the ball of valve 34 is accordingly pushed against its seat. Pressure exerted by capacitor 38 also forces fluid through passageway 30 which is time-delayed by resistor 36, the flow rate of fluid through passage 24 being accordingly greater than that of passageway 30. The continued squeezing and releasing of the pump bulb 12 will transfer all fluid from cuff 16 (or any portion thereof) to the space 38A shown in FIG. 3 and FIG. 4 between diaphragm 38 and the wall of control assembly 14.

When sufficient volume is removed from cuff 16 to release occluding pressure on the urethra, the patient can void. The urethra will remain open until the cuff 16 is refilled. This happens as follows: pressure in cavity 38A being greater than pressure in the pump bulb 12 and cuff 16, fluid is forced through fluid resistor 36 into passageway 24 and upstream into the cuff. If pump bulb 12 is collapsed from its final squeeze, fluid will also flow downstream through passageway 24 and through valve 28 into pump bulb 12. Fluid will continue to flow from cavity 38A (which gradually shrinks to its nondistended form) into both the cuff 16 and pump bulb 12 until both are filled, i.e. until the pressure of the system is equalized. The filled cuff being returned to its inflated state, the urethra is once again occluded.

Figure 3:
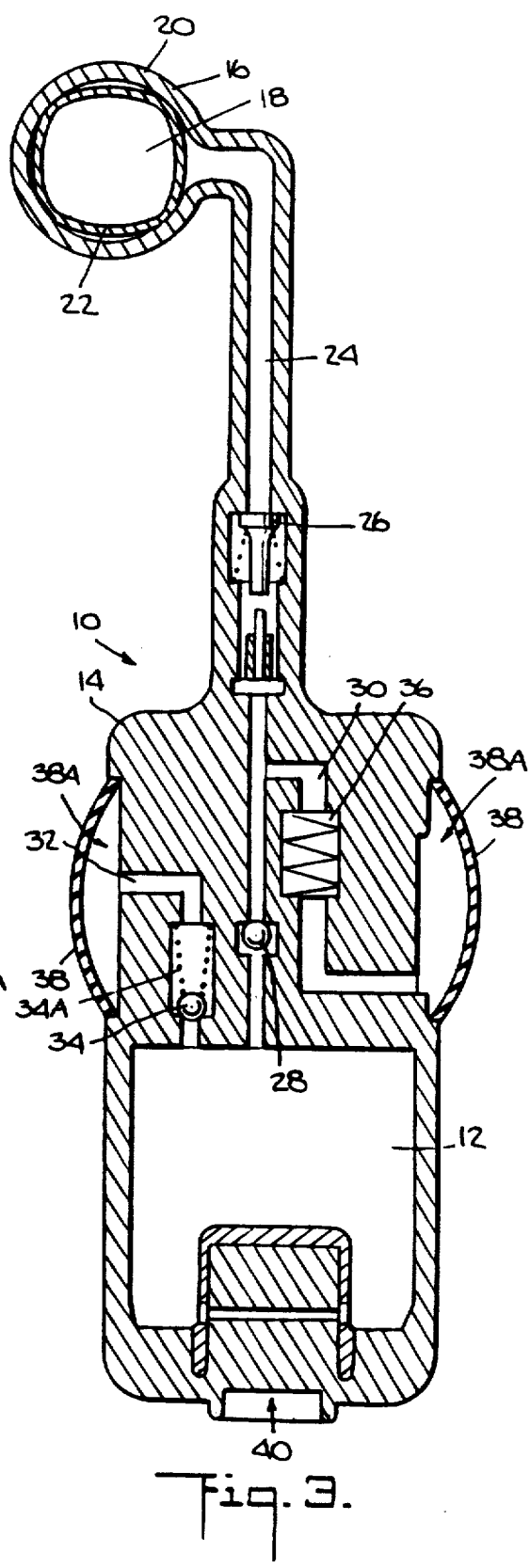
FIG. 3 illustrates the implantable sphincter in accordance with the preferred embodiment of this invention, similar in all respects to FIG. 1, but showing the fluid capacitor in distended form.

In FIGS. 3 and 4, the fluid capacitor 38 is depicted in fully distended form, with space 38A disposed as indicated, and with the cuff 16 deflated and the urethra open. Thus without the need for a bulb reservoir or other distally located component, e.g. in the abdomen, the ordinary function of excretion is carried out utilizing a few simple and small sized components. The system of this invention thus has the virtue of simplicity and the great advantage of reducing the need for serious surgery due to the size, complexity, and number of components.

However, other advantages are also achieved by this invention. It can happen that when the bladders of incontinent people are subjected to long duration pressure of moderate intensity, (e.g. 60–70 cm of H2O), caused by the prolonged pressure increase in the abdominal area or by concomitant bladder overfill, or involuntary bladder contraction, a degree of urine leakage will occur. However, with most presently described artificial sphincters this leakage will not occur because the cuff will not receive a signal to deflate upon the onset of such stimulus. The urethra will remain occluded. As a consequence, urine refluxing and/or restriction of blood outflow and blood supply to the occluded urethra may occur. The sphincter system of the subject invention, on the other hand, is designed to enable the cuff to at least partially deflate and the urethra to thereupon open (thus permitting the flow of a small volume of urine) upon the onset of such long duration, moderate intensity pressures. The way this happens is as follows: upon the advent of such stimulus, the fluid in the system will start to flow downstream into passageways 24 and 30. In the larger passageway 30, the flow will be impeded by the resistor element 36 but eventually, because of the long duration of the pressure surge, the fluid will find its way through this element into the fluid capacitor. When a pressure of predetermined extent is reached, the fluid capacitor will thereupon distend because, as shown in FIG. 1, passageway 30 has a segment, represented as area 30A, which is adjacent to and substantially coextensive with the distensible membrane of fluid capacitor 38. As a consequence even moderate, (but long duration) pressures will suffice to distend the capacitor because the effect thereof will be exerted along almost the entire surface of the membrane (from segment 30A). This will at least partially deflate the cuff and open the urethra to the extent that the required small amounts of urine will exit or "leak". When the pressure in the urethra caused by the long-duration, moderate pressure subsides, fluid from the capacitor will return to the cuff in the previously described manner and the cuff will be reinflated.

However, the sphincter system of this invention will also act to inhibit undesirable involuntary urine leakage when the incontinent person is subjected to high intensity, short-duration pressure "spikes" which can occur following a sudden pressure increase in the abdominal area because of a burst of coughing, laughing, or as stated before, when the person merely lifts a heavy object. In presently described artificial sphincters, this kind of short intensive bursts of pressure will often trigger the involuntary partial deflation of the cuff causing the urethra to open and urine to pass out of the person. However, the present system will inhibit this deflation up to a predetermined and safe level of pressure in the abdominal area and/or the bladder, in the following manner: when the pressure "spike" occurs, there is a short pumping action exerted on the cuff; the flow of fluid downstream will pass through check valve 28 into the pump bulb 12, and also into the larger passage 30. In the latter passageway the resistor element 36 will "hold up" the fluid. Because of the short duration of the "spike" the pulsed fluid will lose its impetus and not reach the fluid capacitor with sufficient pressure to distend the capacitor. However, the flow of fluid through check valve 28 into the pump bulb 12 and upsteam through valve 34 will also enter the narrow passageway 32. However, because of the very narrow area of the passageway 32, the fluid capacitor 38 will also not distend. This is because the pressure "spike" (provided it is less than a predetermined limit), will not (in the short duration of time) be able to exert sufficient force through the narrow passageway 32 to effect distension. In principle, this would be analogous to trying to open a door with one finger.

Thus the sphincter system of this invention through the configuration of the openings of the passageways 32 and 30, and the capacitor design and the relationship of the valves through the control assembly 14, will serve to open the urethra when the body is subjected to predetermined, moderate intensity pressures, of a long, but also predetermined duration, but will serve to keep the urethra closed when the body is subject to high-intensity short duration pressure "spikes", to a pre-established limit. The latter limit is desirable because for extremely high pressure spikes, i.e. on the order of 200 cm of water or greater, it will be prudent to have the urethra open. In the practice of this invention, it can be seen that passageway 30 is pressure-time dependent, while narrow passageway 32 is primarily only pressure-dependent.

Figure 7:
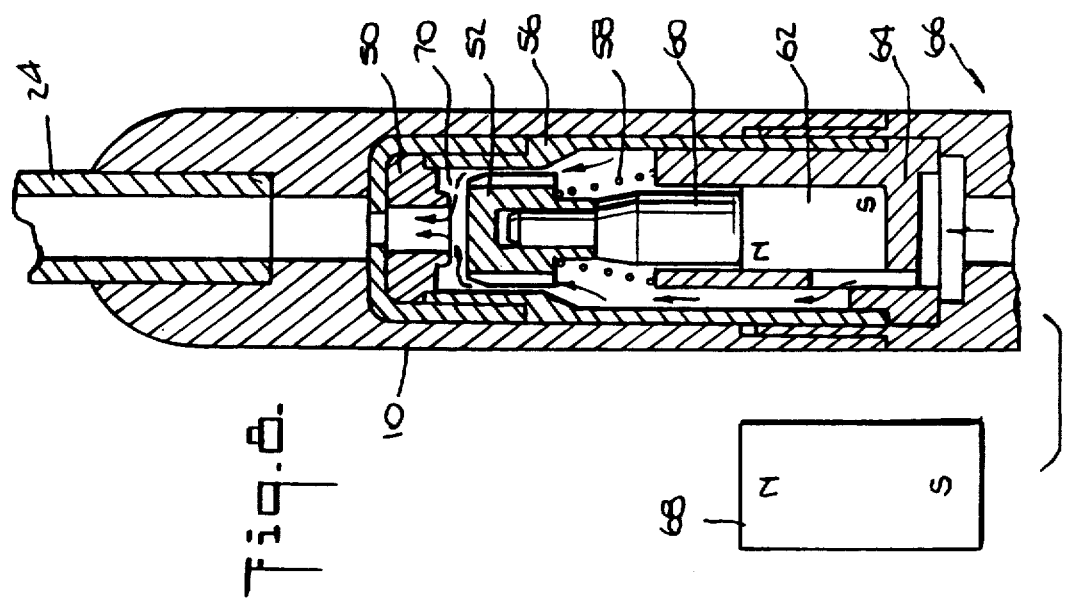
FIG. 7 is a side vertical section of an externally operated magnetic deactivation valve, depicted in closed position.

As previously mentioned, in the main passageway 24 a deactivating valve 26 can be optionally disposed to effect the activation-deactivation of the system when such is deemed necessary, particularly in that postoperative period when the urethra (or other body passage) is greatly sensitive to occlusive pressure due to the trauma of the operation. In this period, it will be desirable to leave the cuff deflated so it does not compress or occlude the urethra. It will also be desirable to have the means to shut the system down, when the patient is unconscious, or when for some reason he or she cannot voluntarily manipulate the pump bulb in order to carry on normal excretory functions, or when the patient is using a catheter. Thus the deactivation valve 26 has substantial value. While any suitable type valve which can be operated externally of the patient can be employed, in the practice of this invention it has been found that a magnetic valve, as hereinafter described, is particularly effective. This valve is described specifically in FIGS. 7 and 8. In this regard, FIG. 7 represents the magnetic valve in its closed position. At the top thereof can be seen passageway or tube 24 through which the fluid to or from the cuff 16 flows as shown in FIG. 1. Within the valve housing, cap 48 surrounds and is contiguous with valve seat 50. Poppet 52 is shown tightly abutting with the seat 50 through seal ring 54. In this closed position, fluid cannot pass upstream, and the sphincter system of the invention is thus deactivated, if fluid is evacuated from the cuff into the capacitor. The rest of the valve encompasses the inner features of the valve, as shown. In this regard, housing 56, spring 58, magnetic still rod 60, internal magnet 62, magnet holder and rod guide 64 and valve cap 66 complete the components of the valve. An external magnet 68, schematically drawn, is also shown.

Figure 8:
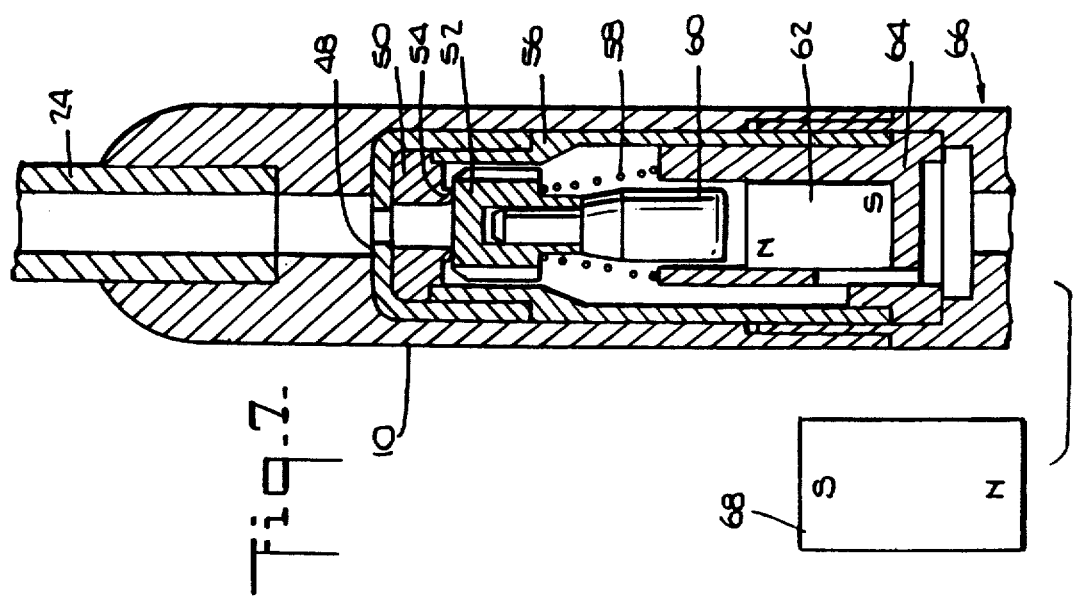
FIG. 8 is a similar view of the magnetic valve of FIG. 7, depicted in open position.

It should be noted that in this closed position, the permanently-aligned north-south magnetic poles of the internal magnet 62 are opposite to those of the depicted external magnet 68, the latter being shown in south-north configuration. In the "open" position, as shown in FIG. 8, i.e. in the activation mode, the internal magnet (which is stationary) is shown as having pulled the magnetic still rod and the compression spring 58 downward thus opening up the passage 70 to the flow of fluid. Arrows depicting the flow (upward) are shown, but the fluid flow can also be downstream as well. In FIG. 8, the disposition of the external magnet is changed from FIG. 7; the poles thereof are shown as being aligned with the poles of internal magnet 62.

In operation, to deactivate the valve 26, external magnet 68, which is stronger magnetically than internal magnet 62 is placed at or near the skin of the person, proximal to the valve 26. When the poles of the external magnet are opposite to the poles of the internal magnet the magnetic force field of the latter is lessened so that it no longer has sufficient force to counteract the strength of the spring 58. The magnetic still rod is thus pulled away from the internal magnet, and the poppet is moved upwards to abut with the seal ring 54 thereby closing the valve and preventing the flow of fluid in the system. The sphincter device is thus deactivated.

When the poles of the external magnet are placed in the the same north-south alignment as the internal magnet 62, the magnetic force of the latter is enhanced; its strength is now stronger than the spring 58. The magnetic still rod is now attracted strongly to the internal magnet, and the poppet 52 is then pulled away from seal ring 54, thus opening the passageway 70. The system is now activated. The valve will stay in the open position with no gap between the internal magnet and magnetic rod, since the attraction force of the internal magnet is larger than the separation force being asserted by the compressed spring. This will continue until the need arises for deactivation.

The internal and external magnets must have sufficient strength to activate and deactivate the valve and are deployed empirically to determine the effective distance for activation and deactivation. It has been found that magnets made of neodymium having an energy product in the range of 34–40 MGO are particularly suitable.

Figure 6:
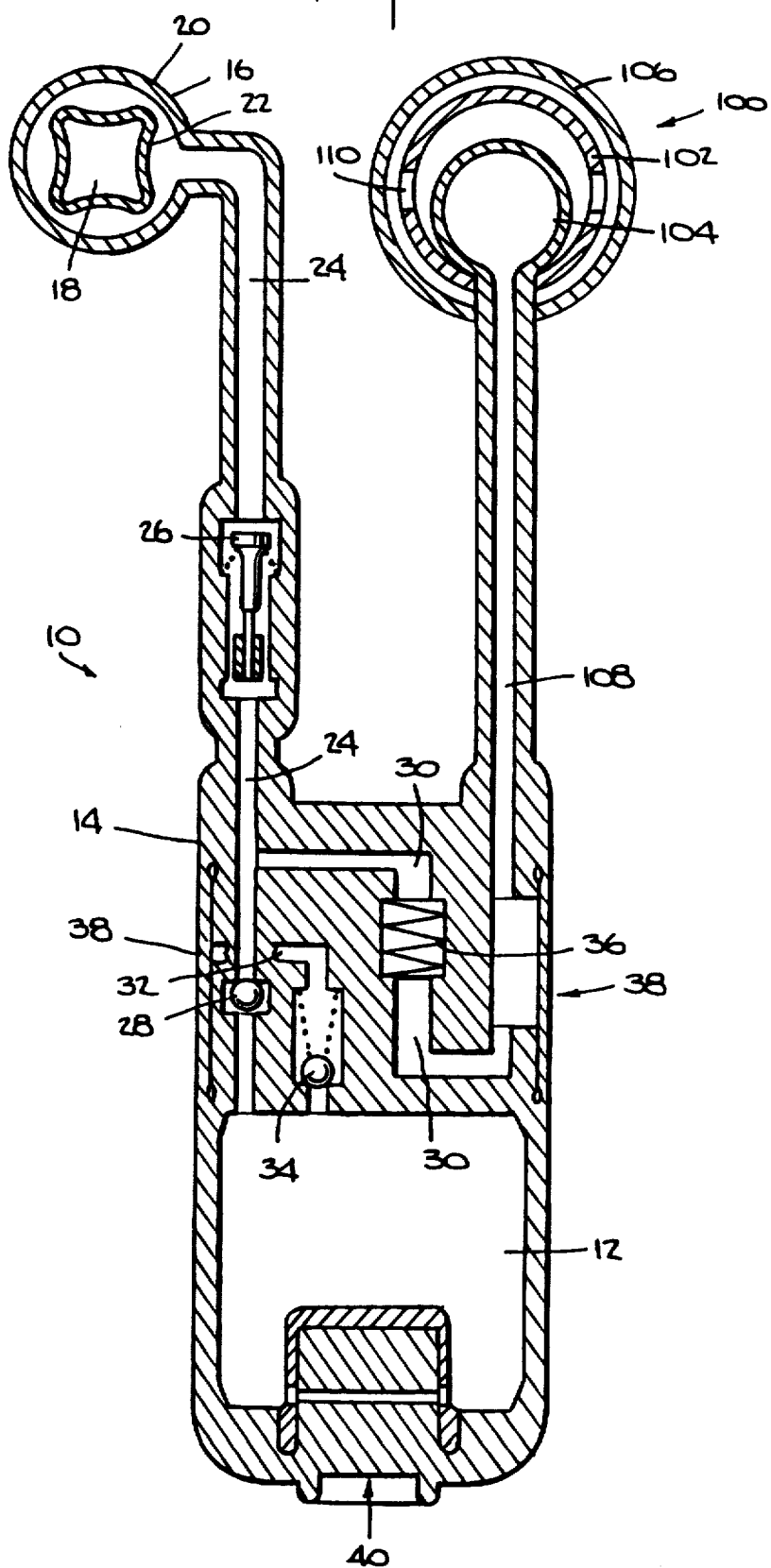
FIG. 6 is another embodiment of the implantable system of this invention illustrated partially in vertical section, which includes a volume compensator in fluid communication with the cuff, pump, control assembly, and fluid capacitor.
Figure 9:
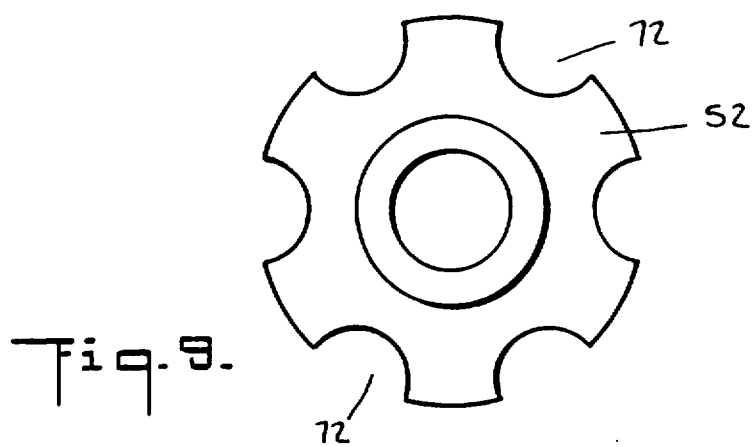
FIG. 9 is a plan view of the poppet of the magnetic valve of FIGS. 7 and 8.

As shown in FIG. 9, in top view, the poppet 52 is seen as having longitudinal channels 72 which permit sufficient fluid flow therethrough when the magnetic valve is in the open position. It should also be noted that the design of the valve overcomes the tendency of the magnetic force exerted by the external magnet to swerve and perhaps jam the magnetic rod-poppet assembly. In passing it should be noted that for illustration purposes only, magnetic valve 26 is depicted in FIG. 1 and FIG. 6 as being in the open, activated position, while in FIG. 3 it is depicted in the closed, deactivated position.

Figure 10:
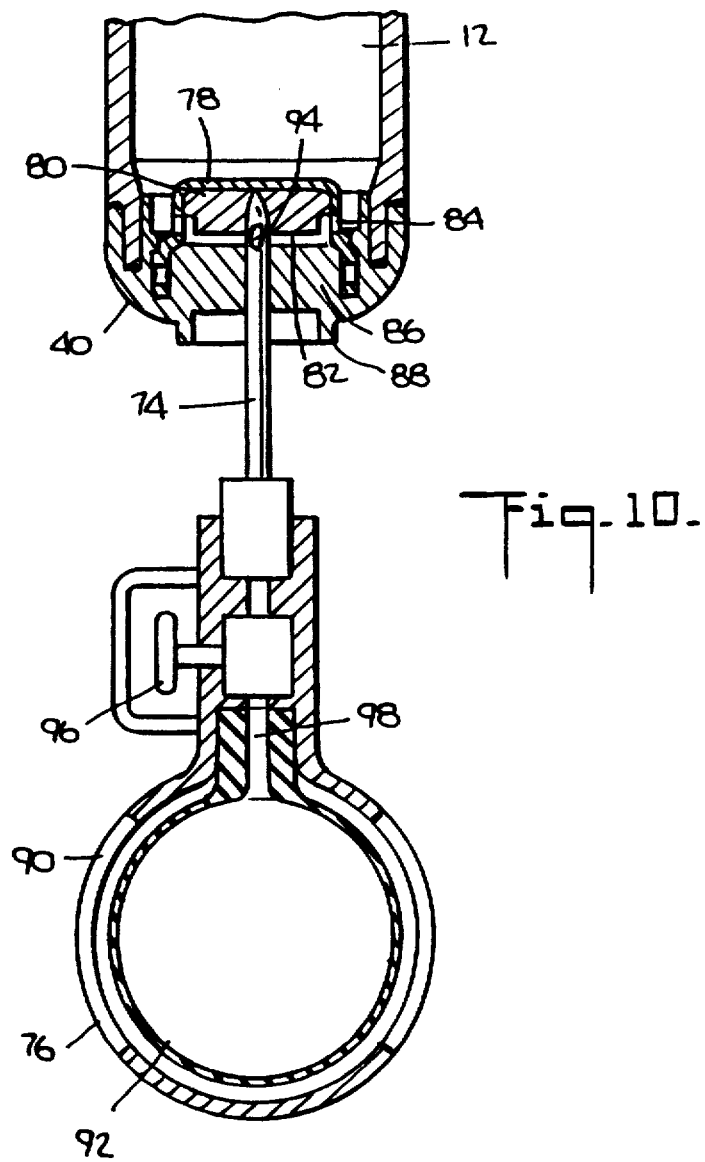
FIG. 10 is a vertical view showing the insertion of a hydraulic needle into the septum of the implantable sphincter system of this invention.

In the practice of this invention it is preferred to use a septum 40, referred to in FIG. 1, as a means for having fluid withdrawn or introduced into or from the sphincter system. As such the pressure of the system can be measured, monitored and adjusted as desired by the attending physician or other responsible person. FIG. 10 depicts a typical septum in the act of receiving a hypodermic needle 74. As shown, septum 40 includes a cap 78 which is rigid and prevents the needle from piercing the inner space of the pump bulb 12, and a small septum 80 which is tightly encased by the rigid septum cap 78. At the base of the small septum is a gap 82 which includes a gap hole 84 which is in fluid communication with pump bulb 12. The septum 40 is made of a self-sealing material such as silicone rubber which is designed to re-seal the hole made by the needle 74 when the latter is withdrawn. The rigid septum cap 78 keeps the section 86 of the septum under compression so that self-sealing can take place. Outer guide ring 88 is disposed at the bottom of the septum to enable the needle to be inserted at a suitable place in the septum.

Hypodermic needle 74 is in fluid communication with an outside pressure adjustment source 76 which includes, as shown in FIG. 10, a housing 90 and an inner fluid-containing pressure adjustment balloon 92 which keeps fluid under a constant but predetermined pressure. Needle 74 contains side holes 94 for enabling fluid to be dispensed therefrom. When inserted into the septum, said holes 94 are aligned with gap (or side vents) 82. In operation, fluid is injected or withdrawn from the needle 74 from side holes 94 into or from gap 82 by opening valve 96 of the fluid source 76. Fluid will then enter or exit from balloon 92 through channel 98. Whether fluid will be withdrawn or introduced into the system will depend on whether the pressure of the system is less than that of the balloon 92 (in which case fluid will be introduced), or more than that of the balloon (in which case fluid will be let out of the system).

As stated previously, the system 10 has a predetermined pressure which is determined by the volume and compliance of the system. Only the capacity of the cuff changes. This change in capacity of the cuff is largely determined by the size of the urethra which varies from patient to patient, and can change in the life of the patient due to the urethra becoming atrophied, or because of other causes such as surgery. The change in the cuff capacity or volume thus causes a change in the entire system's pressure. It is therefore desirable to have the volume of the system adjustable in accordance with the size of the urethra and the concomitant volume of the cuff. The pressure and volume of the system are thus interdependent. The septum 40 enables a doctor to establish the pressure needed to have the sphincter function and enables him to monitor the pressure of the system after the sphincter has been implanted.

FIG. 5 depicts the environmental displacement in a male of the sphincter system of this invention showing the implantation of the pump bulb 12 and the control assembly 14 in the scrotum and the deactivation valve 26 upstream thereof. Cuff 16 is shown circumferentially surrounding the urethra 18 for occlusion thereof and is in fluid communication with the scrotum-implanted components through the fluid passageway 24.

FIG. 6 is another manifestation of this invention which is useful when and if the urethra is atrophying particularly after surgery. When this occurs more fluid is needed to effect occlusion. It differs from FIG. 1 in the inclusion of a volume compensator 100 which comprises a rigid shell 102, a compensator balloon 104, and an outer flexible shell therefor 106. The balloon 104 is in fluid communication with fluid capacitor 38 through passageway 108. The outer flexible shell 106 is in fluid communication only with the rigid shell 102 through holes 110. It should be stressed that the volume compensator 100 is not analogous to the bulb reservoirs of presently available sphincter systems because it is implanted in the scrotum (or analogous area) and not in the abdomen as are most of such reservoirs, and in that the volume of the compensator balloon 104 is limited by the rigid outer shell 102. The pressure which the balloon 104 can exert is proportional to the balloon volume but in contrast to the embodiment of this invention which does not have a volume compensator (wherein a very small change in volume can effect significant changes in pressure), in this embodiment (i.e. with a volume compensator) the pressure of the system is less sensitive to volume change. After the balloon is inflated to the limits of the rigid shell, pressure increases dramatically with almost no volume change. The pressure of the sphincter system is not controlled by the compensator in contrast to the prior described reservoirs, but as stated the pressure of the system is determined by the urethra size and total fluid volume in the sphincter system. The volume compensator depicted in FIG. 6 is also significantly smaller than the reservoirs of the presently available or described artificial sphincters. Therefore, it is possible for it to be placed in the scrotum of male patients. The fluid volume in the balloon 104 will not be the same for every patient but is dependent on the established pressure of the system. In general, to deflate the cuff in this embodiment, most of the fluid is still transferred from the cuff to the fluid capacitor.

The normal operation of the embodiment represented by FIG. 6 is essentially the same as that of the preferred embodiment represented by FIG. 1. That is, the pressing of pump bulb 12 will force liquid up through check valve 34. The fluid will pass through passageway 32 into the capacitor 38. As the pump is then released, allowing the pump bulb to return to its original dimension, fluid will be drawn from the cuff 16 through passageway 24, through valve 28 into pump bulb 12. This fluid transfer will continue as long as the pump bulb is actuated until the cushion 22 of cuff 16 is deflated.

The main function of the volume compensator is to minimize sphincter pressure changes when the urethra diameter changes such as when the latter atrophies or is atrophying. When this occurs, as stated, the capacity of the cuff will also increase. In systems where the volume compensator is not present, even a slight volume change can effect dramatic changes in pressure. For varying reasons, it may not be desirable to adjust the pressure of the system by injecting fluid therein through the septum. If the volume compensator is in the system, as in this embodiment, it may not be necessary to do this. Instead, when pressure drops in the cuff because of the atrophied or atrophying urethra, the pressure of the volume compensator, which becomes higher than that of the cuff, "compensates" by sending fluid back into the system and through passageway 30 up into the cuff, thus maintaining the proper inflation of the latter, and continuing the occlusion of the urethra.

It is apparent that modifications and variations besides those specifically mentioned herein may be made in the structures and techniques described herein and depicted in the accompanying drawings without departing from the concept of the present invention. For example, while the magnetic valve embodiment is depicted as being applicable to the sphincter system of this invention, it can also be used in conjunction with any hydraulic sphincter device.

I claim:

1. An implantable sphincter system for reversibly occluding a body passageway, which comprises
a fluid inflatable occlusion means adapted to substantially encircle a body passageway, a control assembly in fluid communication with said occlusion means, said assembly including a fluid capacitor disposed thereon for storing of fluid when said occlusion means is deflated, said capacitor being capable of distending under fluid pressure and
a pump means in fluid communication with said occlusion means for transferring fluid from said occlusion means to said capacitor to deflate said occlusion means and open said body passageway, said occlusion means and said fluid capacitor to deflate said occlusion means and open said body passageway, said occlusion means and said fluid capacitor being connected such that said occlusion means remains substantially inflated during short, significant pressure increases in said body passageway up to a predetermined limit, but wherein said occlusion means at least partially deflates on prolonged moderate pressure increases in said body passageway.

2. A sphincter system according to claim 1 wherein said fluid capacitor includes a flexible membrane capable of distending under fluid pressure.

3. A sphincter system according to claim 1 or 2, wherein said system includes a fluid resistor for restricting the flow of fluid from said occlusion means to said fluid capacitor.

4. A sphincter system according to claim 3 wherein said fluid capacitor is connected with said occlusion means through a first fluid passage and through a second fluid passage, said second fluid passage being in fluid isolation from said first fluid passage and including said fluid resistor.

5. A sphincter system according to claim 4 wherein the fluid pressure required to distend said flexible membrane is higher on fluid connection through said first fluid passage than on fluid connection through said second fluid passage.

6. A sphincter system according to claim 2 wherein said pump means is adapted to be penetrated by a hollow needle without loss of fluid pressure within said sphincter system.

7. A sphincter system according to claim 6 wherein said pump means includes a septum which may be penetrated by a hollow needle without loss of fluid pressure within said sphincter system.

8. A sphincter system according to claim 5 wherein the first fluid passage is pressure dependent, while the second fluid passage is pressure-time dependent.

9. A sphincter system according to claim 1 wherein a valve is situated between said occlusion means and the remainder of said system for breaking the fluid communication between said occlusion means and said remainder of said system on closing said valve.

10. A sphincter system according to claim 9, wherein the valve includes a magnet having fixed polar alignment, which magnet acts to open or close the valve when the magnetic field thereof is strengthened or weakened as a consequence of a second magnetic field directed at such magnet from an externally disposed magnetic source.

11. A sphincter system according to claim 10, wherein said external magnetic source is a magnet adapted to be held outside of the surface of a body containing the passageway to be occluded, in close proximity to the internally disposed magnet of the valve.

12. A sphincter system according to claim 1 or 2, wherein, in a male, the fluid capacitor and pump are adapted to be implanted substantially within the scrotum of such male, and the body passageway is the urethra.

13. An implantable sphincter system for reversibly occluding a body passageway, which comprises
   a fluid-inflatable occlusion means adapted to substantially encircle a body passageway,
   a fluid capacitor in fluid communication with said occlusion means for storing of fluid when said occlusion means is deflated, said capacitor being capable of distending under fluid pressure,
   a pump means in fluid communication with said occlusion means for transferring fluid from said occlusion means to said capacitor to deflate said occlusion means and open said body passage, said occlusion means and said fluid capacitor being connected such that said occlusion means remains substantially inflated during short, significant pressure increases in said body passage up to a predetermined limit, but wherein said occlusion means at least partially deflates on prolonged moderate pressure increases in said body passage, and
   a volume compensator means in fluid communication with said occlusion means and said capacitor for compensating change of volume in the sphincter system such that said occlusion means on said change of volume is capable of occluding said body passage on fluid inflation, the fluid pressure in said occlusion means being substantially the same before and after said change in volume.

14. A sphincter system according to claim 13 wherein said volume compensator comprises a flexible inner balloon located within a rigid enclosure and a flexible outer shell surrounding and in fluid communication with said rigid enclosure.

15. A sphincter system according to claim 14 wherein said fluid capacitor includes a flexible membrane capable of distending under fluid pressure.

16. A sphincter system according to claim 15 wherein said system includes a fluid resistor for restricting the flow of fluid from said occlusion means to said fluid capacitor.

17. A sphincter system according to claim 16 wherein said fluid capacitor is connected with said occlusion means through a first fluid passage and through a second fluid passage, said second fluid passage being in fluid isolation from said first fluid passage and including said fluid resistor.

18. A sphincter system according to claim 17 wherein the fluid pressure required to distend said flexible membrane is higher on fluid connection through said first fluid passage than on fluid connection through said second fluid passage.

19. A sphincter system according to claim 15 wherein said pump means is adapted to be penetrated by a hollow needle without loss of fluid pressure within said sphincter system.

20. A sphincter system according to claim 19 wherein said pump means includes a septum which may be penetrated by a hollow needle without loss of fluid pressure within said sphincter system.

21. A sphincter system according to claim 17 wherein the first fluid passage is pressure dependent, while the second fluid passage is pressure-time dependent.

22. A sphincter system according to claim 13 wherein a valve is situated between said occlusion means and the remainder of said system for breaking the fluid communication between said occlusion means and said remainder of said system on closing said valve.

23. A sphincter system according to claim 22 wherein the valve includes a magnet having fixed polar alignment, which magnet acts to open or close the valve when the magnetic field thereof is strengthened or weakened as a consequence of a second magnetic field directed at such magnet from an externally disposed magnetic source.

24. A sphincter system according to claim 23 wherein said external magnetic source is a magnet adapted to be held outside of the surface of a body containing the passageway to be occluded, in close proximity to the internally disposed magnet of the valve.

25. A sphincter system according to claim 13 or 15 wherein, in a male, the fluid capacitor and pump are adapted to be implanted substantially within the scrotum of such male, and the body passageway is the urethra.

26. An implantable sphincter system for reversibly occluding a body passageway, which comprises,
   a fluid inflatable cuff adapted to substantially encircle a body passageway,
   a control assembly downstream from said cuff and in fluid communication therewith, said assembly including a fluid capacitor disposed thereon for storing of fluid when said cuff is deflated and which is capable of distending under fluid pressure, and further including first and second fluid passages which are in fluid isolation from each other within said assembly,
   a pump means in fluid communication with said cuff through said assembly, for transferring fluid from said cuff to said fluid capacitor through said first and second fluid passages to deflate said cuff and open said body passageway, wherein the pressure required to distend said fluid capacitor on fluid connection through said first fluid passage is higher than the pressure required to distend said fluid capacitor on fluid connection through said second fluid passage.

27. A sphincter system according to claim 26 wherein said fluid capacitor includes a flexible membrane capable of distending under fluid pressure, and said second fluid passage includes a fluid resistor for restricting the flow of fluid from said occlusion means to said fluid capacitor.

28. A sphincter system according to claim 27 wherein said pump means includes a septum which may be penetrated by a hollow needle without loss of fluid pressure within said sphincter system.

29. A sphincter system according to claim 28 wherein a valve is situated between said occlusion means and the remainder of said system for breaking the fluid communication between said occlusion means and said remainder of said system on closing said valve, said valve including a magnet having fixed polar alignment, which magnet acts to open or close the valve when the magnetic field thereof is accordingly strengthened or weakened as a consequence of a second magnetic field directed at such magnet from an externally disposed magnet held outside of the surface of a body containing the passageway to be occluded.

30. An implantable sphincter system according to claim 1 wherein the fluid capacitor is circumferentially disposed about said control assembly.

31. An implantable sphincter system according to claim 26 wherein the fluid capacitor is circumferentially disposed about said control assembly.

32. A valve for opening or closing a hydraulic sphincter system which comprises a housing which includes therein, a valve seat, a poppet, spring means for exerting a force on said poppet which would normally keep the poppet in abutting relationship with said valve seat thereby placing the valve in a closed mode, and an internal magnet having fixed north-south polar alignment which when said valve is in a closed mode exerts insufficient magnetic force on the poppet to overcome the force being asserted by the spring means;

but wherein the magnetic force of said internal magnet is enhanced to the extent necessary to overcome the force from said spring by virtue of a further magnetic field originating from an externally disposed magnetic source whose poles are in the same alignment as that of the internal magnet, thereby pulling said poppet away from said valve seat to abut with said internal magnet thereby placing the valve in an open mode, said valve being then capable of staying in said open mode until the magnetic field of said internal magnet is weakened to the extent wherein the force thereof is insufficient to overcome the force of said spring means by the further application of an external magnetic source the polar alignment of which is opposite to that of the internal magnet, thereby displacing the poppet and placing the valve in its closed mode.

* * * * *

UNITED STATES PATENT AND TRADEMARK OFFICE
CERTIFICATE OF CORRECTION

PATENT NO. : 4,994,020
DATED : Feb. 19, 1991
INVENTOR(S) : Mark Polyak

It is certified that error appears in the above-identified patent and that said Letters Patent is hereby corrected as shown below:

Claim 1, Column 10, lines 9-12, delete "said occlusion means and said fluid capacitor to deflate said occlusion means and open said body passageway,"

Signed and Sealed this

Twenty-sixth Day of October, 1993

Attest:

BRUCE LEHMAN

Attesting Officer

Commissioner of Patents and Trademarks